United States Patent [19]

Pierangela et al.

[11] Patent Number: 6,054,030

[45] Date of Patent: Apr. 25, 2000

[54] SYSTEM FOR MONITORING BIOCIDE TREATMENTS

[75] Inventors: Cristiani Pierangela, Cernusco sul Naviglio; Mollica Alfonso; Ventura Giovanna, both of Genoa, all of Italy

[73] Assignee: Enel S.p.A., Rome, Italy

[21] Appl. No.: 08/873,590

[22] Filed: Jun. 12, 1997

[30] Foreign Application Priority Data

Jun. 28, 1996 [IT] Italy .................................. MI96A1330

[51] Int. Cl.[7] .................................................. G01N 27/26
[52] U.S. Cl. ........................................ 204/404; 205/775.5
[58] Field of Search .................................. 204/404, 403; 205/778.5, 779, 777.5, 775.5, 776; 324/71.1, 72, 439

[56] References Cited

U.S. PATENT DOCUMENTS

| | | | |
|---|---|---|---|
| 3,337,798 | 8/1967 | Twinning et al. | 205/776 |
| 3,951,161 | 4/1976 | Rohrback et al. | 137/3 |
| 5,356,521 | 10/1994 | Nekoksa et al. | 205/775.5 |

FOREIGN PATENT DOCUMENTS 405107217  4/1993  Japan .

OTHER PUBLICATIONS

Derwent abstract of JP 405107217 A, Apr. 27, 1993.
Derwent abstract of JP 405107217 A, Apr. 27, 1993.
p. 244 of Davies et al. "A Dictionary of Electrochemistry", John Wiley & Sons, N.Y., 1976).

"Innovation and Technology Transfer for Corrosion Control", 12 pages, 11th International Corrosion Congress, 4.333, vol. 4, 1990, Month Unknown, Dexter et al., "Effect of Biofilms On Corrosion Potential . . . ".
Florian Mansfeld et al., "A Technical Review of Electrochemical Techniques Applied to Microbiologically Influenced Corrosion", pp. 247–272, Corrosion Science, vol. 32, No. 3, 1991, Month Unknown.
G.J. Licina et al., "Experience with On–Line Monitoring of Biofilm Activity in Power Plant Environments", 12 pages, Structural Integrity Associates, Inc., Mar. 1994.
A. Mollica et al., "Corrosion in Natural and Industrial Environments: Problems and Solutions—International Conference", pp. 249–255, Nace International Italia Section in Cooperation with Associazino Italiana di Metallurgia, 1995, Month Unknown, "On the Mechanism of Oxygen Reduction Potential . . . ".
L. Giuliana, "On–Line Monitoring of Aerobic Bacteria to Optimise Chlorine Injection", 8 pages, ATEL s.r.l.–Italy, (1993 date not sure).

*Primary Examiner*—T. Tung
*Assistant Examiner*—Alex Noguerda
*Attorney, Agent, or Firm*—Young & Thompson

[57] ABSTRACT

A probe is conveniently positioned in a flowing aqueous medium. The probe is formed by two electrodes of notable difference in nobility connected by an electric resistance high enough to ensure that the voltage difference between its terminals is sufficiently great to permit accurate and simultaneous determinations of the growth of biofouling and the chlorine concentration by measuring the potential difference variations between the terminals.

11 Claims, 3 Drawing Sheets

SYSTEM FOR MONITORING BIOCIDE TREATMENTS

The present invention concerns a system for monitoring biocide treatments.

FIELD OF THE INVENTION

The invention concerns a biocide treatment monitoring system that makes possible the simultaneous control of:

a) the growth of biofouling on metallic structures, b) the oxidant concentration in the water.

More particularly, the invention concerns a system for controlling and optimizing biocide oxidizing treatments by monitoring the growth of biofouling on the piping and other metallic parts of industrial plants and controlling the concentration of the oxidants present in the water along the cooling circuits in the course of the oxidizing biocide treatments.

It is well known that plants and cooling circuits employing natural water in which biofouling occurs call for periodic cleaning interventions.

In particular, as an example of installations in which the biofouling phenomenon has to be reduced or eliminated mention may here be made of thermoelectric and nuclear power stations, oil installations, the chemical plants of the food and paper industry and water pipelines in general.

In this context it should be briefly recalled that biofouling comprises "microbiofouling" and "macrobiofouling". Simplifying the matter, microbiofouling, the field in which the present invention is situated, may be said to consist of bacteria and microalgae immersed in an organic matrix (biofilm) that englobes also inorganic deposits, corrosion products and other materials.

All types of immersed materials become colonized by microorganisms and covered by biofilm, even though there exist considerable differences of microbic composition, thickness and development time of the microfilm according to the compounds present on the surface of the substrate and the roughness of this surface, the temperature, the hydrodynamics of the site, etc. Microbiofouling induces marked chemical and physical modifications of the surfaces of metallic materials capable of passivation and as a general rule compromises their capacity of resisting corrosion.

Microbiofouling constitutes the first stage of the growth of biological fouling and acts as growth substrate for the macroscopic component of biofouling, the socalled "macrobiofouling" (for example: crustaceans, molluscs, vegetal matter, etc.). Unlike microfouling, its macroscopic counterpart forms very substantial incrustations that can cause the total or partial occlusion of pipes, render structures considerably heavier and produce an extremely high roughness coefficient that—in the case of ships—implies a significant increase in specific fuel consumption. Furthermore, macrobiofouling can accelerate the corrosion phenomena of metals, because it creates regions of differential aeration, deposits, occlusions and tubercles distributed in a non-uniform manner over the wetted surface.

A negative effect deriving from the presence of microbiofouling inside the tubing of industrial heat exchangers is constituted by the diminution of the heat exchange, which significantly, reduces the efficiency of the equipment and, in the case of thermoelectric power stations, can bring in its wake a significant increase in specific fuel consumption.

The biofouling phenomenon is strongly influenced by the geographic and climatic characteristics of the site that hosts the plant in question, and this is particularly true as far as the growth of macrofouling is concerned. The fouling phenomena are particularly marked in marine environments.

For these reasons industrial plants and works that make use of natural waters and suffer from the problems induced by biofouling have to be subjected to biocide treatments of adequate efficacy to inhibit the development of the phenomenon and to guarantee a certain degree of cleanliness of the wetted surfaces.

STATE OF THE ART

The biocide treatments most commonly employed in industrial sector cooling circuits are based on the use of chlorine, especially in the form of sodium hypochlorite and other chlorine compounds, chlorine dioxide being a case in point.

Normal present-day practice sees biocide treatments carried out in conformity with standardized specifications or consolidated practices based on acquired experience. The times to be employed and the biocide concentrations are rarely chosen in the light of the results of at least a temporary local monitoring of the biological and chemical biofouling growth parameters. For these reasons the treatments often prove to be either ineffective or excessive.

More recently, thanks to research into microbiological corrosion, various electrochemical systems have been developed for monitoring the growth of microbiofouling in metal pipes. Though for the most part still experimental, the new instruments employ sampling probes inserted in the cooling circuits and work by evaluating the evolution of the corrosion processes sustained by the growth of bacteria at the metal-biofilm interface by means of continuous measurement of a number of electrochemical parameters (current density, electrode potential, impedance, electrochemical noise, polarization resistance) of which the variations have been found to be directly connected with the growth of the biofilm at the metal-water interface.

As far as measurement of the oxidant concentration in the water is concerned, the methods derived from conventional analytical chemistry have long since become consolidated in the case of discontinuous measurements. When continuous measurements have to be made, on the other hand, especially in sea water, the instrumentation used for this purpose is of relatively recent origin and is associated with limitations and problematics that it is now proposed to discuss.

A) We shall commence by mentioning the known instruments for monitoring the growth of microfouling based on electrochemical systems.

The starting point for the design of electrochemical biofilm probes is constituted by the observation that the formation of biofilm on a series of alloys of the active-passive transition type (stainless steels, titanium, copper alloys) causes an increase in the oxygen reduction kinetics (depolarization of the cathode process) on the surface of these alloys, thereby rendering natural water more corrosive than sterile "artificial" water.

An evaluation of the rate of oxygen reduction can therefore provide a measure of the greater corrosiveness induced by the formation of biofilm on a series of alloys and consequently, albeit indirectly, also a measure of the development of biofilm on an electrode.

The instrumentations so far developed exploit the fact that the kinetics of the cathode process can be readily quantified by, for example, using a potentiostat to determine the density of the current that passes through an electrode maintained at a given cathode potential. The increase in the current density absorbed by the electrode can be directly linked to the bacterial activity on the electrode surface.

A first type of known probe is the one called BIO-GEORGE (due to Structural Integrity Associates—U.S.A.) and consists of two electrodes in the form of 304 L stainless steel discs that, by means of an instrumentation external to the probe, are differently polarized for brief periods (half an hour per day, for example). The growth of biofilm on the surface of the electrodes is correlated with the increase of the polarization resistance of the electrodes and induces significant increments of the polarization current or potential; furthermore, it will also generate a current or potential after the polarization has been removed and these, in turn, will provide further information about the biofilm formation.

The probe is of small size and is sold together with the polarization apparatus and, on request, the data acquisition system.

The principal drawbacks of this probe are that it measures only the growth of biofouling, considers the presence of an oxidant (chlorine or its derivatives, for example) as an interference signal, carries out only very discontinuous measurements (one per day), involves rather long and pre-determined waiting times (about half an hour) before the measurements become available, and uses sophisticated instruments (potentiostats, etc.) for carrying out the measurements.

A second type of known probe is the one known as "BIOGUARD System" (by ATEL). This system utilizes probes consisting of two tubular steel samples, respectively AISI 316 L austenitic stainless steel and carbon steel, galvanically coupled via an electrical resistance of very small value (1–10 Ohm). In these conditions the potential of the stainless steel electrode becomes displaced in the cathodic direction, while the carbon steel electrode behaves like a sacrificial anode. The galvanic coupling current is sustained by the cathode processes that occur at the interface between the metal and the biofilm on the stainless steel sample and by the gradual dissolution of the carbon steel. The probes are designed to work in a range of potentials in which the formation of the biofilm causes currents of relatively high intensity.

The current intensity variations measured in the course of time can be correlated with the growth of the biofouling on the surface of the probe.

The current circulating in the probe is measured by short-circuiting the resistance between the electrodes (with instruments of the zero-resistance ammeter type). In the commercial system, which makes continuous measurements, the resistance between the electrodes of the probes is permanently short-circuited and the intensity of the resulting current, subject to the presence of biofouling on the probe, is very high for the entire functioning period of the equipment.

The probe is associated with a current-reading device and is integrated into a system complete with pumps and relays to control the pump that doses the biocide.

The principal disadvantages of this probe are as follows: it measures only the growth of biofouling and is not capable of evaluating the oxidant addition on account of the high current produced by the probe (the presence of an oxidant, like chlorine or its derivatives, is detected only as a very slight interference signal); the nobler electrode (referred to also as the working electrode) suffers marked carbonization phenomena, so that the probe must either be frequently cleaned with acid or, alternately, replaced at short intervals of time; the sacrificial carbon steel electrode corrodes very quickly and in a nonhomogeneous manner, so that the probe has to be frequently replaced, often after the occurrence of a short circuit between the two electrodes caused by the corrosion products, which interferes with the reliability and significance of the measurements.

The following patent applications made in Italy are also known: Nos. 22141, 22142 and 22143 of Oct. 26, 1989.

The applicants are also aware that a patent has been granted for an electrochemical method of measuring the growth of biofouling on stainless steel surfaces based on an estimate of the galvanic coupling current or potential differences between two identical electrodes, where biofouling is allowed to grow on one electrode, while the other is maintained clean by means of a high-speed current of water. The second or reference electrode is realized as a moving component of a pump inserted in the water circulation circuit (and therefore in continuous contact with fast-flowing water).

The principal and specific problems of the solutions just indicated are as follows: they consider only biofouling monitoring; they consider the effect of the oxidant in the water as an interference and not as a parameter to be evaluated; the reference electrode is completely dependent on the continuous operation of a pump.

B) We shall now proceed to examine the systems for the "continuous" analysis of chlorine (or other oxidants).

The permissible chlorine concentration in industrial effluents in the various European (and extra-European) countries is usually subject to more or less restrictive limits imposed by law. In Italy, for example, the law regulating industrial wastes sets an upper limit of 0.2 ppm of active chlorine when the effluents are discharged into natural environments (sea or inland fresh waters).

The carrying out of chlorine-based biocide treatments therefore calls for very careful control of the doses employed, and this not only with a view to avoiding waste, but also and above all to avoid exceeding the legal discharge limits. On the other hand, the chlorine concentration in the water cannot be determined by estimating the input product quantities, because the chlorine (or other oxidizing agent) becomes rapidly reduced by the organic substances present in the water and its concentration diminishes continuously as a function of the contact time and the quantity of organic (or oxidizable) matter present in the body of water subjected to treatment. Efficacious biocide treatments therefore call for a continuous evaluation of the chlorine demand of the water to be treated and knowledge of the contact times of the biocide in the given volume of water. Alternatively, one would have to carry out continuous measurements of the chlorine concentration at various points of the volume of water to be treated while the treatment is actually in course.

The biocide concentration that can react with the biofouling established on the surfaces of industrial installations is thus a function of the biocide previously consumed in the water, the chlorine demand of the water and the contact times.

In fresh water, the hydrolysis of chlorine gives rise mainly to hypochlorous acid, ie.:

$$Cl_2 + H_2O = HClO + H^+ + Cl^- \qquad (1)$$

In sea water, on the other hand, the conspicuous presence of the halides $I^-$ and $Br^-$ implies the formation of hypobromous and hypoiodous acid:

$$HClO + Br^- = HBrO + Cl^- \qquad (2)$$

$$HClO + I^- = HIO + Cl^- \qquad (3)$$

On the basis of the facts just outlined, it is common practice to speak of a Total Residual Chlorine concentration (abbreviated as T.R.C.) when making measurements in fresh water, whereas in sea water reference is made to the socalled Total Residual Oxidant concentration (abbreviated as T.R.O.).

As far as the applicants are aware, in commerce there are today available a number of automated systems for measuring the chlorine (concentration in the water that are derived from the traditional iodometric technique, i.e. transforming the residual chlorine in the water into iodine by means of the addition of known quantities of iodide and then measuring the iodine (or iodine/iodide) concentration present in the water.

$$Cl_2 + 2I^- = 2Cl^- + I_2 \quad (4)$$

$$ClO^- + 2I^- + 2H^+ = Cl^- + I_2 + H_2O \quad (5)$$

The interferences are the same as are associated with all the iodine titration methods and are constituted by the oxidizing agents that convert the iodide into iodine (oxygen, bromine, iodates, copper ions, dioxides of manganese, etc.).

The present state of the art knows electrodes for "continuous" chlorine measurements conceived for measurements in water mains and in fresh water. From these there have been developed versions suitable also for sea water, but almost all of these require the water to be appropriately treated before the meeasurements can be carried out.

The principal systems for continuous measurements of the chlorine (defined as Total Residual Oxidant) are usually divided into two types: ammeter methods and potentiometer methods, both derived from the respective conventional analysis methods. By way of example, we shall now describe some types of probe known to the applicant.

Ammeter probe with membrane.

This probe is provided with a semipermeable membrane at its tip immersed in the water to be (continuously) analyzed. This membrane permits chlorine and bromine to diffuse into the internal solution.

The internal solution contains potassium iodide, which reacts in stoichiometric quantities with any chlorine or bromine that migrates across the membrane and thus becomes oxidized into iodine.

The principal drawbacks of these membrane-type systems and probes make themselves particularly strongly felt in the case of sea water measurements, given the fact that the sample has first to be treated. More particularly, the membrane is subject to fouling and wear problems; the measurement is not really "continuous", but rather takes the form of a series of successive punctiform measurements (one every ten minutes, for example) on account of the delay caused by the need for pretreating the sample and the time that passes before an equilibrium becomes established in the solution within the membrane; the measurement suffers significantly from a certain drift of the reference base line due to various concomitant factors; it also requires the user to keep the reagent consumption and the proper functioning of the reagent dosing system. Lastly, the measurements call for a frequent revision of the calibration curves.

Membraneless ammeter probe with flow cell.

Many of the problems associated with membrane-type ammeter probes have been overcome by abolishing the membrane and introducing a flow cell in which the electrodes are directly immersed. In, this case the current flowing between the electrodes will vary as a function of the various forms of oxidized halides present in the water flowing through the cell (T.R.O) and not of the sole $I_2$ species, though to a certain extent this goes to the detriment of the accuracy and sensitivity of the measurement.

As far as; the measurement of the T.R.O. in solution is concerned, this type of probe is the one that presents most analogies with the probe of the system according to the invention, from which it differs by virtue of the fact that the flowing current derives from the potential actively imposed by the electronic instrumentation connected to the probe, whereas in the system according to the invention the current derives passively from the galvanic coupling of the electrodes (numerous other differences derive from the choice of the materials of the electrodes and the shape of the cell, which is simpler and more economic in the system according to the invention).

Potentiometer probe.

The probe in this case consists of two electrodes, a platinum electrode and an electrode selective with respect to iodide ions, immersed directly in the solution to be analyzed, which is automatically pretreated with stoichiometrically defined quantities of potassium iodide and acetic acid.

The redox potential of the $I^-/I_2$ couple is measured in the solution to be analyzed; the potential difference between the two electrode, is correlated with the iodine concentration in the solution (by means of Nernst's law).

The instrument may also be equipped with a temperature correction probe.

This probes functions in the same conformation in both fresh and sea water.

The principal disadvantages derive from the need for: pretreating the water sample to be analyzed; having to check the reagent consumption and the proper functioning of the reagent dosing system; rather frequently repeating the calibration curves with water samples to be analyzed; compressing the information into a rather narrow range of values, of the order of about 30 mV every ten ppm (in other words, per logarithmic concentration unit).

The General Disadvantages of the State of the Art

We can now summarize the general disadvantages associated with the known systems and items of equipment as follows:

There do not exist any techniques capable of monitoring biofouling and the T.R.O. concentration with a single instrument.

The existing instruments for monitoring one or other of these parameters are either costly or require frequent maintenance and sometimes do not provide reliable information (especially in sea water).

In the case of the existing biofouling monitoring techniques and equipments, for example, it is generally considered that the presence of an oxidant in the water constitutes an interference with the current (or voltage) measurement, because the oxidant acts on the cathode characteristics of the system and produces the same effect as the biofouling.

Brief Summary of the Invention

The system according to the invention, which can be said to be a particular and simplified application of the ammeter technique, comprises an electrochemical probe or sensor made up of a working electrode, a sacrificial electrode, and an electrical resistance connecting the two electrode. As characterized in the claims, the working electrode is made of a noble metal, while the sacrificial electrode consists of a less noble metal (reference being here made to the scale of the galvanic series of the elements) and the resistance is high enough to make it possible to obtain an accurate measure of the T.R.O. concentration and the growth of aerobic biofouling on the nobler electrode by measuring the potential difference between the two terminals of the resistance. This probe or sensor can be said to be of a "mixed type", because it is sensitive not only to the growth of the aerobic biofouling, but also to the residual oxidant in the water. It goes without saying that the probe will have to be positioned in the aqueous medium to be monitored in such a manner as to ensure that it will be in contact with a continuous flow of the water to be analyzed. The very small electric current that flows in a passive manner in the probe, in the absence of electrical instrumentation (as in the case of the traditional ammeter technique for measuring the T.R.O. only), derives from the specific nature of the electrodes, the value of the electric resistance interposed between the electrodes, and the geometric conformation of the electrodes.

The system will preferably comprise also the following:
a) a means of acquiring, continuously processing and graphically displaying the data provided by the sensor;
b) a means of commanding the commencement or termination of biocide immission into the water to be treated and modification of the concentration of the biocide employed for the treatment.

It is to be understood that the means indicated in a) and b) above are readily available as conventional processing equipment (complete with appropriate software).

It has been found experimentally that with an initial voltage between the resistance terminals of at least 0.4 V (in the absence of biocide and biofilm) the probe is capable of:
signalling T.R.O. variations in the range between 0.1 and 1.0 ppm with a good degree of accuracy, and
signalling the establishment of biofouling right from the early phases of the process in the form of a voltage variation between the resistance terminals.

Appropriate modifications of the resistance also make it possible to increase the sensitivity of the fouling measurements as compared with that of the chlorine measurements.

The working electrode will preferably be made of special stainless steel or titanium, while the sacrificial electrode is of zinc.

Preferably, too, the two electrodes will be tubular elements placed at a suitable distance from each other on the same longitudinal axis, so that they will be crossed by the water flow and will therefore be particularly suitable for developing desired signals in contact with the water.

The following may also be comprised in the system as additional characteristics:
d) a pump to ensure water flow along the electrode axis when there is no natural flow,
e) a flow measuring device for correct evaluation of the parameters that depend on the flow,
f) a water temperature measuring device to eliminate possible interferences with of the measurement, and
g) an auxiliary probe to measure solely the T.R.O. concentration.

The principal purpose of the system according to the invention is therefore that of optimizing the oxidizing biocide treatments by means of an evaluation of the growth of biological microfouling on a sample probe and the evaluation of the T.R.O. concentration to be found in the water during the course of biocide treatments. The system is particularly suitable for sea water treatments, but, given the innovative characteristics of the probe, it can also be used in solutions having a higher resistivity than sea water; consequently, there are no counterindications as regards its use in other types of water, fresh water being a case in point.

Advantages of the Invention

The advantages of the invention are rather numerous; the most important one is fact that the growth of microfouling and the residual oxidant concentration (T.R.O.) in water treated with oxidizing biocides can be monitored with a single item of equipment. Additional advantages derive from the installation of this system on all plants and installations affected by biofouling problems can be summarized as follows:

1. real time control of biofouling growth;
2. the quantity of sodium hypochlorite (or of other oxidizing agents) that has to be employed in order to obtain an efficacious T.R.O. concentration in the water can be determined in real time without having to carry out continuous chemical analyses to determine the chlorine demand and concentration, thereby avoiding also the use of costly instruments that require careful and frequent maintenance (T.R.O analyzers of a conventional type) and, as compared with such instruments, there is also the fact that the water samples do not have to be subjected to any preliminary treatment prior to analysis (thus avoiding also the use of reagents);
3. optimization of the consumption of sodium hypochlorite (or of other oxidizing agents), limiting this consumption to the times arid concentrations strictly necessary to ensure cleanliness;
4. as compared with similar known probes, the probe according to the invention ensures minimal consumption of the sacrificial electrode, i.e. of the less noble metal, and therefore a much longer life of the probe, just as it prevents carbonation of the nobler electrode; lastly, the probe according to the invention can be used also in natural waters less conductive than sea water; and
5. The zinc used for the sacrificial electrode dissolves slowly in the water and thus automatically ensures that it will always remain clean and efficient.

DETAILED DESCRIPTION OF THE INVENTION

The innovative aspects of the invention would appear to be the following:

1. the measuring probe with its own electrodes and resistance,
2. the experimental relationship that links the increment in the potential difference between the terminals of the resistance connecting the two electrode and the effective T.R.O. concentration in the water to be analyzed, and
3. the use of accessory probes to amplify the details of the measurements.

Figure 1:
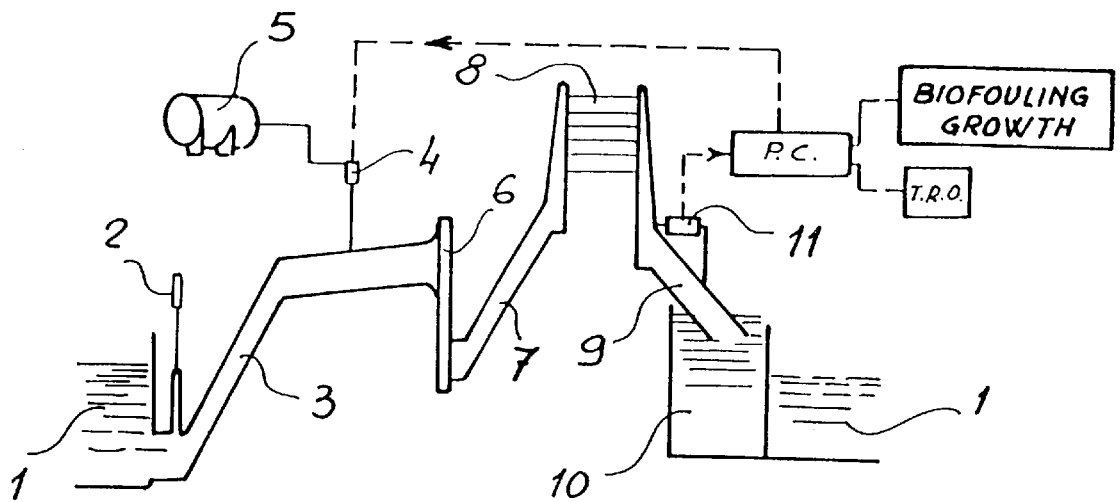
FIG. 1 shows a general layout of the system.

FIG. 1 schematically shows an example of how the system can be used in a thermoelectric power station. The layout is almost self-explanatory: the water flow to be monitored is obtained by means of a pump 2 from a sea water reservoir (1) and passes through a channel 3 into which a pump 4 introduces an appropriate quantity of sodium hypochlorite contained in a tank 5; a rotating grid 6 filters the water before it passes through the channel 7 into a condenser 8, subsequently to be discharged through a discharge duct 9 into a channel 10 that takes it back into the sea water reservoir 1. From the discharge duct 9 there is branched off a quantity of water that is made to pass through the probe according to the invention 11, which will be described in detail by reference to FIG. 2; a personal computer PC equipped with appropriate software acquires the data from the probe 11, which it then processes in such a way as to indicate the growth of the biofouling and the total residual oxidant T.R.O. and it also controls the pump 4, starting and stopping it as required.

Figure 3:
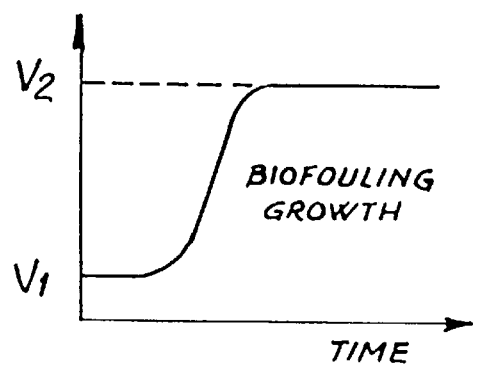
FIGS. 3–8 show various voltage curves plotted against time.
Figure 4:
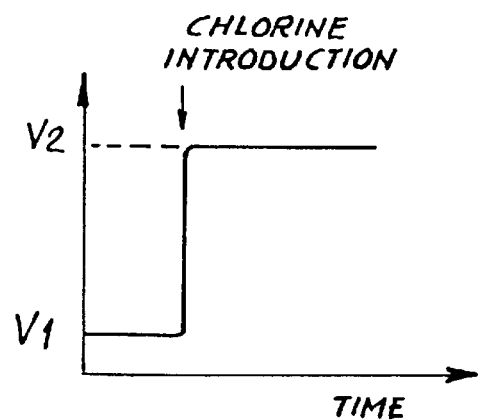

The functioning of the system is based on the fact that, in a given potential interval, both the addition of an oxidant (chlorine, for example) and the growth of biofouling on the surface of the working electrode will modify the kinetics of the cathode process in the electrochemical probe, producing an increment of the potential difference between the resistance terminals, although they will do so in different ways and, above all, at different rates (FIGS. 3 and 4).

Analyzing the time pattern of the potential difference between the resistance terminals (preferably by means of an appropriate software), it is therefore possible to pinpoint and display in graphic form the time patterns of the T.R.O. concentration and the biofouling growth on the nobler electrode.

Figure 2:
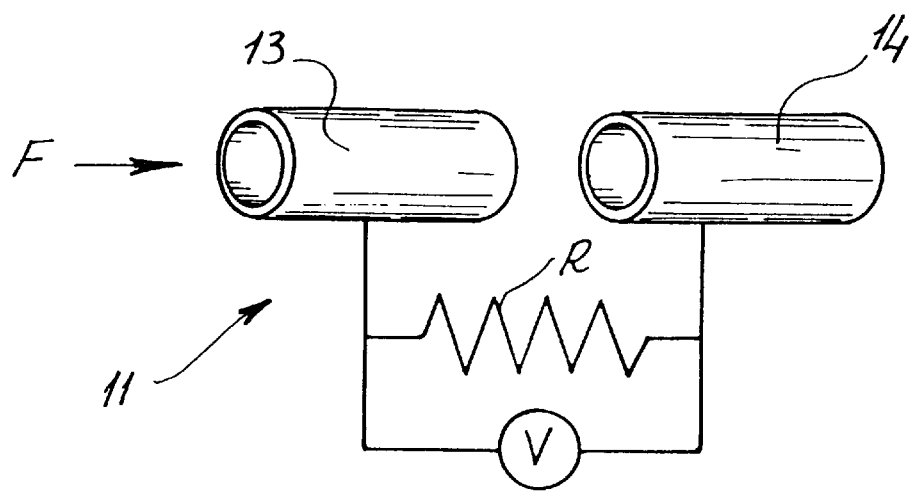
FIG. 2 shows a detail of the electrodes.

By way of example and in schematic form, FIG. 2 shows a probe or sensor consisting of a working electrode in special stainless steel 13 arranged at an appropriate distance from a sacrificial zinc electrode 14; the two electrodes are crossed by the treated water (fresh or sea water, provided that it is conductive) at a rate of about 1 m/s and are connected by an electrical resistance R of such value as to provide a potential difference V of at least 0.4 V between the resistance terminals. The direction of the water flow F is such as to make the water pass first through the working electrode and then the sacrificial one. The two electrodes have an internal diameter of 25 mm and a length of about 100 mm.

The form and the disposition of the electrodes will be chosen in such a way as to adapt the instrumental arrangement in an optimal manner to the characteristics of the plant and the aqueous medium to be monitored.

The current density of the cathode process on the noble element of the probe should be limited to a very low value, of the order of 0.1–1.0 $\mu A/cm^2$, say, thereby determining also the potential variations of the working (or nobler) electrode.

Examples of the Use of the Invention

Measurement of biofouling growth and T.R.O concentration with a single probe.

The growth of biofouling, just like the addition of an oxidant to the water, causes the cathode curve of the probe or sensor to become displaced in the same direction in which it will be displaced by an oxidant addition, as shown in FIGS. 3 and 4.

FIG. 3 shows how the voltage between the resistance terminals varies during the growth of the biofouling; at first, when there is no biofouling, this voltage maintains a low base value, but as the bacteria begin to grow, it will increase and eventually reach a final value corresponding to the complete establishment of the biofouling, i.e. when it covers the entire surface of the working electrode.

FIG. 4 illustrates the voltage variations between the resistance terminals following the introduction of the chlorine into the solution; it can be seen that in this case the voltage variation is instantaneous.

The substantial difference between the two phenomena lies in their respective action times on the working electrode.

In the case of an oxidant addition to the water there is an immediate electrode response, while the working electrode response times in the case of biofilm growth are considerably slower, because—starting with a clean electrode—it may take several days before the electrode becomes completely covered. In normal operating conditions of the monitoring equipment, therefore, it is readily possible to distinguish between the contribution that the two phenomena make to the signal.

Figure 5:
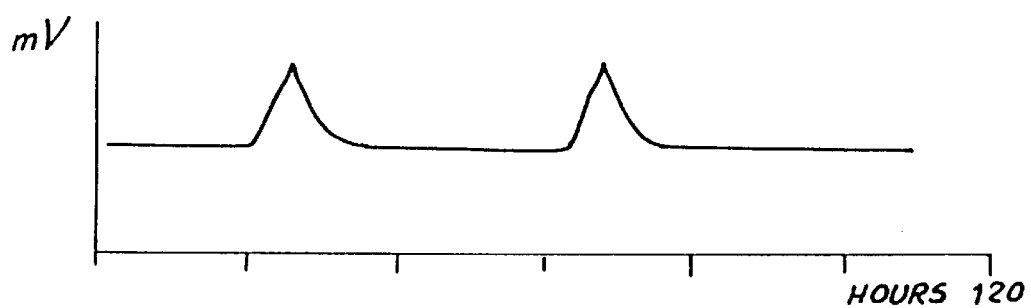
Figure 6:
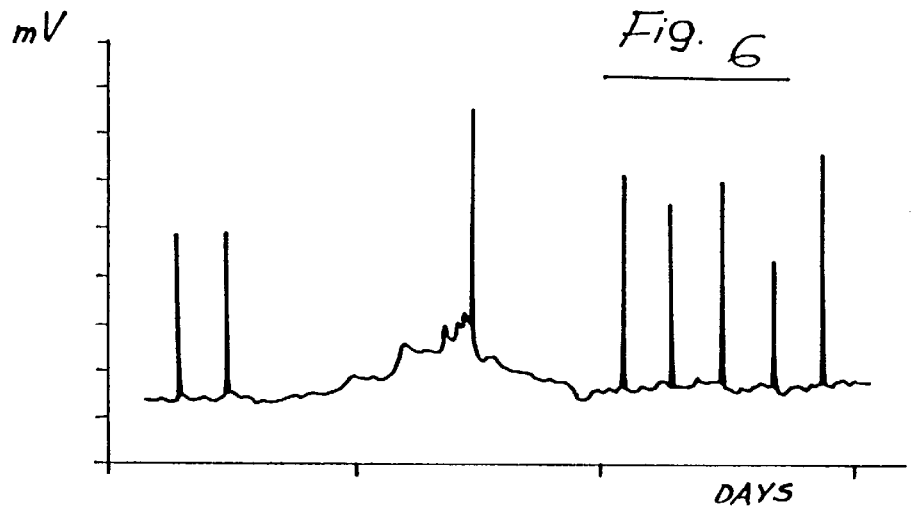

In actual practice, for as long as the probe remains relatively clean, in the course of chlorinations for example, the variations of the potential difference will be primarily a function of the residual oxidant concentration in the water, as illustrated by FIG. 5, which shows the signal pattern of the probe in the case of discontinuous chlorination and in the absence of biofouling. When efficacious and intermittent chlorination cycles are carried out, the signal pattern will reveal a base line that will tend to drift due to the effects of the biofouling, and from this base there will depart a series of peaks caused by the residual oxidant in the water, as can be seen from FIG. 6, which reproduces the signal pattern of a probe at a thermoelectric power station: the peaks correspond to chlorination,; of a duration of the order of half an hour at a concentration variable between 0.4 and 1.0 ppm of T.R.O. The increase in the base line value corresponds primarily to fouling growth; the chlorine concentration can be readily obtained from the height of the peaks, while the drift of the base line indicates the efficacy of the treatment.

Figure 7:
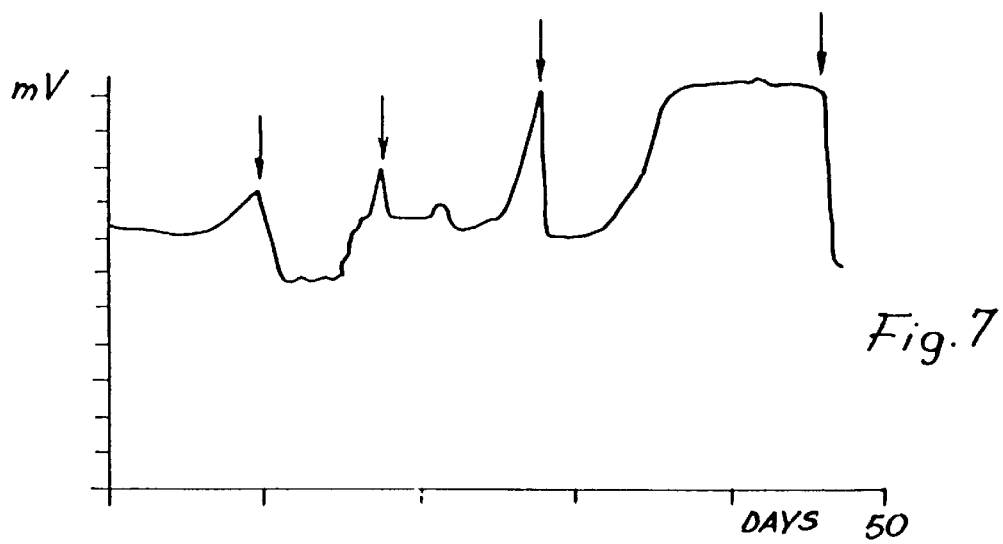

In the absence of an oxidizing treatment, the signal variations in the course of time will generally be slow or follow known patterns of the phenomenon, corresponding exclusively to the growth of the biofouling on the probe (unless there are interferences due to other parameters, which will be discussed separately further on). FIG. 7 shows the pattern of the output signal of the probe in the presence of growing biofouling; the arrows indicate the points where( chlorination operations were performed, but the signal peaks corresponding thereto cannot be seen in this example, because data acquisition was suspended during the chlorinations.

When the system is used for carrying out only occasional biocide treatments, it may happen that some biofouling is already present on the probe, so that the initial output signal will be relatively high; in this situation it will not be possible to make an accurate determination of the oxidant concentration in the water (not only because the biocide will be partly consumed by the biofilm before it arrives at the surface of the probe, but also because the destruction of the biofilm causes a gradual diminution of the output signal). As the chlorination proceeds and probe cleaning is completed, the signal will become stabilized around a value correlated with the oxidant concentration. Knowing the characteristic value of the signal in conditions of absence of biofouling and oxidant treatment, it will again become possible to calculate the oxidant concentration. When these conditions are attained, the information obtained from the monitoring system can be used to interrupt the treatment (manual or automatic shutdown of the oxidant dosing system).

Measurement of biofouling growth and T.R.O concentration with two separate probes.

The use of a single mixed-type probe is normally sufficient for complete monitoring and optimization of the treatment, because the respective contributions to the output signal of the oxidant in the water and the biofouling on the probe can be readily identified.

Nevertheless, in cases where it is desired to obtain accurate control of both parameters in all possible conditions, we world suggest the use of an auxiliary probe (on which the growth of biofouling must be prevented as described below) to monitor only the total oxidant concentration in the water. The separate contribution made by the biofouling can then be determined by analyzing the difference between the signals provided by the two probes.

Figure 8:
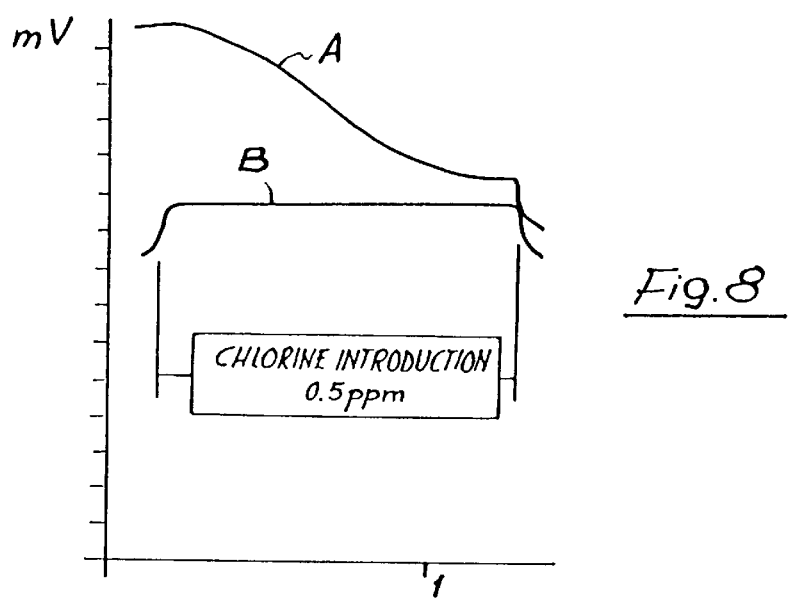

FIG. 8 shows the pattern of the output signal of the two probes in the course of a chlorination at 0.5 ppm; the upper curve (A) represents the output signal of a first probe covered by already established biofouling that becomes removed during the chlorination, as is indicated by the diminution of the signal; the lower curve (B) represents the signal of the clean auxiliary probe kept free of biofilm; in this case, therefore, the signal corresponds only to the chlorine concentration; on completion of the chlorination both probes return to furnishing the initial signal in the absence of both biofilm and chlorine.

In the specific case of chlorination treatments carried out in the cooling circuits of thermoelectric power stations, when the water temperature at the condenser outlet often arrives or exceeds 35–38° C., it is possible, at least in first approximation, to obtain simultaneous measurements of the entity of the biofouling and the chlorine concentration by proceeding as follows: two identical probes are installed respectively immediately upstream of the condenser, where the growth of biofouling is normally greatest, and immediately downstream of it. In these conditions the system will obtain information concerning the growth of the biofouling from the probe upstream of the condenser, while the chlorine concentration can be better determined from the downstream probe. The entity of the biofouling can then be deduced from the difference between the signal patterns on the inlet and outlet sides of the condenser.

Auxiliary probe for total oxidant measurements only

The auxiliary probe in this case is identical to the mixed-type r) robe and is associated with an appropriate accessory device that will keep it free of biofouling in the course of time.

An appropriate accessory device capable of ensuring the cleanliness of the working electrode of the auxiliary probe in sea water could be a small cell producing chlorine by electrolytic means to be installed immediately upstream of the auxiliary probe.

This small-scale chlorine production in the immediate vicinity of the working electrode of the auxiliary probe can inhibit the growth of biofouling on the latter and would have to be considered as an additional constant in the chlorine measurement.

Another way of obtaining the same end could be that of installing an auxiliary probe immediately after the mixed-type measurement probe and equipping the auxiliary probe with a dosing pump to add small quantities of biocide upstream of it, though this system has the disadvantage that small quantities of biocide have to be be kept in store.

However, any other method that will keep the electrodes of the probe free of biofouling can be employed.

Signal interference and measurement limits

The probe measures only the growth of aerobic bacteria. When anaerobic conditions come into being, which can happen under very thick biofilms, errors may be introduced into the measurement.

Flow variations and temperature variations will likewise give rise to signal interference (though of relatively small magnitude), so that it will be desirable to equip the instrumentation with appropriate temperature and flow controls.

Proper functioning of the probe is ensured only by the presence of flow.

As a general rule, it will be desirable to realize and maintain the probe in such a manner as to simulate the conditions of the pipes and the other parts of the installations that are to be monitored for biofouling growth. As far as the actual biofouling measurements are concerned, it should be borne in mind that, just as in other probes already known to the state of the art, the monitoring is performed on the biofouling present on the surface of the working electrode of the probe. The biofilm on the probe may therefore differ in chemical and/or biological composition from the one effectively present in the plant and subjected to the biocide treatment, and there may also be quantitative differences between them.

Turning now to the T.R.O. measurements, the probe is sensitive to the effective concentration in the immediate vicinity of the working electrode.

In the case of a well established biofilm on the working electrode, the chlorine may be consumed before it arrives at the electrode surface; in these conditions it would be advisable to use an accessory probe to measure only the T.R.O.

The claimed invention is:

1. A system for monitoring biocide treatment of an aqueous medium, the system comprising:

a probe comprising a metal working electrode and a sacrificial electrode of a metal less noble than said metal working electrode, said metal working electrode and said sacrificial electrode being exposed in a flowing aqueous medium receiving a biocide treatment;

an electrical resistance connecting said metal working electrode and said sacrificial electrode, said electrical resistance ensuring a passively generated difference between said metal working electrode and said sacrificial electrode of at least 0.4 volts which ensures simultaneous and continuous determination of a biofilm growth on said probe and a chlorine concentration of the flowing aqueous medium;

a processor connected to said probe and acquiring data therefrom, said processor displaying the data and directing start, modification and completion of the biocide treatment based on the data; and an auxiliary probe having two electrodes of different nobility metals that are in the flowing aqueous medium and connected by a further electrical resistance so that said auxiliary probe ensures determination of total oxidant concentration of the flowing aqueous medium, and a device for keeping said two electrodes of said auxiliary probe free of a biofilm.

2. The system of claim 1, wherein said working electrode comprises one of stainless steel and titanium and said sacrificial electrode comprises zinc.

3. The system of claim 1, wherein said working electrode and said sacrificial electrode are straight hollow tubes through which said flowing aqueous medium flows and wherein said straight hollow tubes have a common longitudinal axis that is substantially parallel to a direction of flow of the flowing aqueous medium.

4. The system of claim 3, wherein each of said tubes has a ratio of internal surface area to cross-sectional area of about 16.

5. The system of claim 4, wherein each of said tubes is about 100 mm long and has a diameter of about 25 mm.

6. The system of claim 1, wherein said working electrode is upstream of said sacrificial electrode.

7. A system for monitoring biocide treatment of an aqueous medium, the system comprising:

a dual measurement probe comprising a metal working electrode and a sacrificial electrode of a metal less noble than said metal working electrode, said metal working electrode and said sacrificial electrode being exposed in a flowing aqueous medium receiving a biocide treatment, said metal working electrode and said sacrificial electrode being straight hollow tubes through which said flowing aqueous medium flows, said straight hollow tubes having a common longitudinal axis that is substantially parallel to a direction of flow of the flowing aqueous medium;

an electrical resistance connecting said metal working electrode and said sacrificial electrode of said dual measurement probe, said electrical resistance ensuring a passively generated difference between said metal working electrode and said sacrificial electrode of at least 0.4 volts which ensures simultaneous and continuous determination of a biofilm growth on said probe and a chlorine concentration of the aqueous medium;

an auxiliary probe with two electrodes of different nobility metals that are in the flowing aqueous medium and connected by a further resistance so that said auxiliary probe ensures measurement of total oxidant concentration of the flowing aqueous medium;

a device for keeping said two electrodes of said auxiliary probe free of biofilm; and a processor connected to said dual measurement probe and said auxiliary probe and acquiring data therefrom, said processor displaying the data and directing start, modification and completion of the biocide treatment based on the data.

8. The system of claim 7, wherein said working electrode comprises one of stainless steel and titanium and said sacrificial electrode comprises zinc.

9. The system of claim 7, wherein each of said tubes has a ratio of internal surface area to cross-sectional area of about 16.

10. The system of claim 7, wherein said working electrode is upstream of said sacrificial electrode.

11. The system of claim 7, wherein said further resistance ensures a passively generated difference between said two electrodes of at least 0.4 volts.

* * * * *

UNITED STATES PATENT AND TRADEMARK OFFICE
CERTIFICATE OF CORRECTION

PATENT NO. : 6,054,030
DATED : April 25, 2000
INVENTOR(S) : Pierangela CRISTIANI et al.

It is certified that error appears in the above-indentified patent and that said Letters Patent is hereby corrected as shown below:

On the title page, Item [19], change "Pierangela et al." to --Cristiani et al.--.

On the title page, rewrite Item [75] as follows:

--[75] Inventors: Pierangela Cristiani, Cernusco sul Naviglio; Alfonso Mollica; Giovanna Ventura, both of Genova, all of Italy--.

Signed and Sealed this

Sixth Day of February, 2001

Attest:

Q. TODD DICKINSON

*Attesting Officer*  *Director of Patents and Trademarks*